United States Patent [19]

Kuzma

[11] Patent Number: 5,545,219
[45] Date of Patent: Aug. 13, 1996

[54] COCHLEAR ELECTRODE IMPLANT ASSEMBLIES WITH POSITIONING SYSTEM THEREFOR

[75] Inventor: Janusz A. Kuzma, Englewood, Colo.

[73] Assignee: Cochlear, Ltd., Lane Cove, Australia

[21] Appl. No.: 414,656

[22] Filed: Mar. 30, 1995

[51] Int. Cl.$^6$ .................................. A61F 2/18; A61N 1/00
[52] U.S. Cl. ................................................. 623/10; 607/137
[58] Field of Search .............................. 623/10; 607/137, 607/56, 116

[56] References Cited

U.S. PATENT DOCUMENTS

| | | | |
|---|---|---|---|
| 4,284,085 | 8/1981 | Hansen et al. | 128/784 |
| 4,819,647 | 4/1989 | Byers et al. | 128/642 |
| 4,832,051 | 5/1989 | Jarvik et al. | 128/784 |
| 5,000,194 | 3/1991 | van den Honert et al. | 128/784 |
| 5,037,497 | 8/1991 | Stypulkowski | 156/245 |

FOREIGN PATENT DOCUMENTS

| | | |
|---|---|---|
| 0002068 | 5/1979 | European Pat. Off. |
| 0007157 | 1/1980 | European Pat. Off. |
| 2823798 | 9/1979 | Germany |

OTHER PUBLICATIONS

W. Bruszewski et al., "Injection Molded Structural Spine," 1994 RETEC:R94–034, pp. 2–20 and Figs. 1–12, Studies on Pediatric Auditory Prosthesis Implants, 15th Quarterly Progress Report, Apr. 1, 1994 to Jun. 30, 1994, from Coleman and Epstein Laboratories, University of California, San Francisco.

Kuzma et al., U.S. Pat. Appln. Ser. No. 08/211,269, "Self-Curving Cochlear Electrode Array," filed May 4, 1994.

*Primary Examiner*—Randy C. Shay
*Attorney, Agent, or Firm*—Gottlieb, Rackman & Reisman, P.C.

[57] ABSTRACT

An implantable cochlear electrode assembly includes an initially straight flexible rod-like electrode carrier and an initially straight flexible rod-like positioning member which extend in substantially parallel relation to and closely alongside each other. The assembly is inserted endwise into the scala tympani of the cochlea so as to adopt the spiral curvature of the cochlea, with the positioning member being disposed at that side region of the electrode carrier which faces the outer wall of the cochlea and is opposite to the side region of the electrode carrier at which the contact faces of the array of electrodes are exposed. The electrode carrier and the positioning member are connected to each other at their respective leading and trailing end regions but are separate from and unconnected to each other over their entire medial regions, so that the positioning member can assume an outwardly arched configuration relative to the electrode carrier for forcing the latter into a close hugging engagement with the modiolus and for disposing the contact faces of the electrodes in as close a juxtaposition to the cells of the spiral ganglion as possible. With the trailing end region of the positioning member locked to the trailing end region of the electrode carrier, a stable implantation of the assembly is achieved.

25 Claims, 8 Drawing Sheets

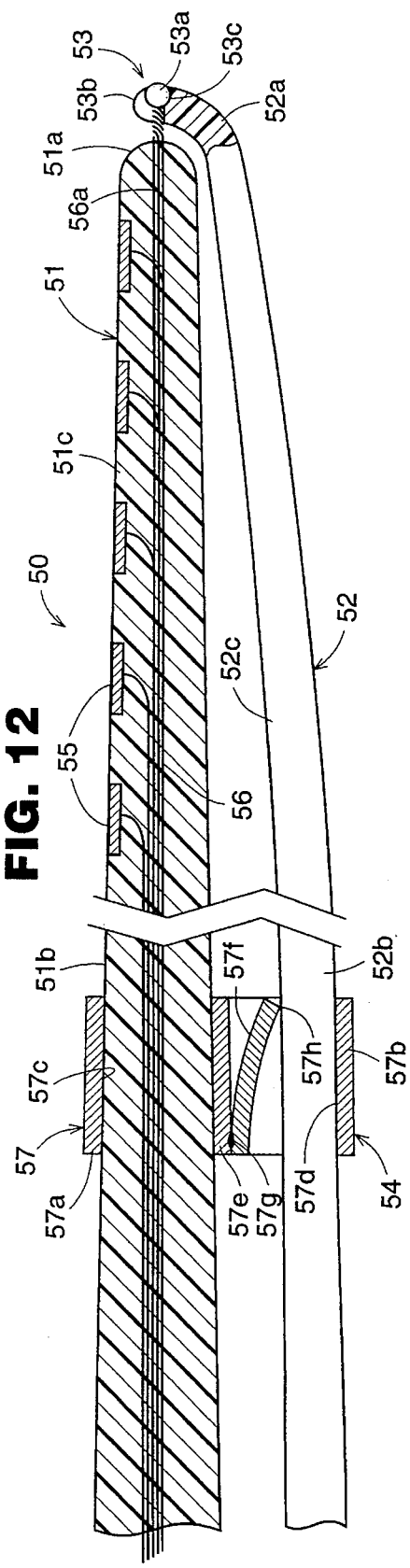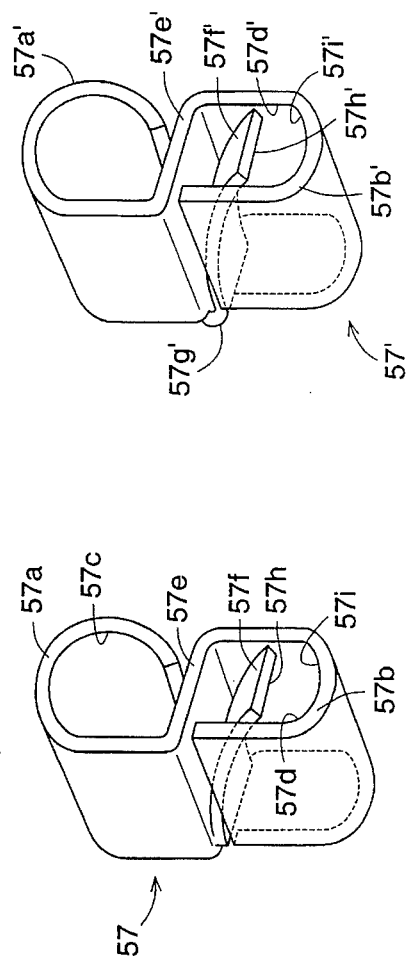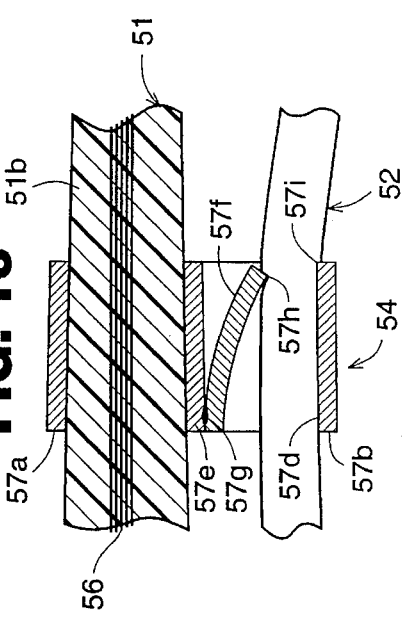

COCHLEAR ELECTRODE IMPLANT ASSEMBLIES WITH POSITIONING SYSTEM THEREFOR

This invention relates to cochlear electrode implant assemblies, and more particularly to a system for optimally positioning an implanted stimulating electrode assembly including an array of electrodes on a carrier therefor in the cochlea of a human ear.

CROSS REFERENCE TO RELATED APPLICATION

The present invention is an improvement over the cochlear electrode implant and in particular over the cochlear electrode positioning system disclosed in a prior copending application Ser. No. 211,269, filed May 4, 1994 in the names of Janusz Kuzma, Henry Lee Seldon and Gordon G. Brown, and entitled "Self-Curving Cochlear Electrode Array."

BACKGROUND OF THE INVENTION

Generally speaking, the portions and structural components of a human ear with which the present invention is most closely concerned, though well known to those skilled in the art, are illustrated diagrammatically (without being drawn precisely to scale) in FIGS. 1A and 1B of the hereto appended drawings. In the human ear 30 (see FIG. 1A) of a normal hearing person, sound impinges on the eardrum 31 and is transmitted into the cochlea 32 via a system of bones 33 called the ossicles, which act as levers to provide amplification and acoustic impedance matching, to a piston or membrane 34 called the oval window. The cochlea 32 is a spirally wound tube, resembling a snail shell, which is about 35 mm long when unrolled and is divided along most of its whole length (see FIG. 1B) by a partition 35 called the basilar membrane. The lower chamber 36 of the cochlea is called the scala tympani, and the upper chamber 37 is called the scala vestibuli. The cochlea is filled with a fluid with a viscosity of about twice that of water. The scala tympani 36 is provided with another piston or membrane 38 called the round window (see FIG. 1A), which serves to take up the displacement of the fluid when the oval window 34 is moved.

When the oval window is acoustically driven via the ossicles 33, the basilar membrane 35 is correspondingly displaced and vibrated by the movement of fluid in the cochlea. The displacement of the basilar membrane stimulates the hair cells 39 which are situated in a special structure 39a on the basilar membrane. Movements of these hairs produce electrical discharges in fibers of the auditory nerve through the intermediary of the cells 40 of the spiral ganglion 41 which are located in the modiolus or modiolar wall 42 at the radially inner wall 43 of the cochlea.

Hearing loss, which may be due to many different causes, is generally of two types, conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds. To overcome this problem, there have been developed numerous cochlear implant systems which seek to bypass the hair cells in the cochlea (the hair cells are located in the vicinity of the radially outer wall 44 of the cochlea) by presenting electrical stimulation to the auditory nerve fibers directly, leading to the perception of sound in the brain and an at least partial restoration of hearing function. The general common denominator in these systems has been the implantation, into the cochlea, of electrodes which are responsive to suitable external sources of electrical stimuli and which are intended to transmit those stimuli to the ganglion cells and thereby to the auditory nerve fibers.

In the known cochlear implant systems, the carrier 45 for the stimulating electrodes 46, as shown in FIGS. 2–7, usually is a slightly tapered straight or minimally curved rod of a cylindrical or part-cylindrical cross-section and is made of a resiliently flexible biocompatible synthetic plastic material such as a silicone polymer available commercially under the name "Silastic". The electrode carrier is surgically placed into the scala tympani, in close proximity to the basilar membrane, and currents passed to the electrodes 46 via respective conductors or leads 47 embedded in the electrode carrier result in neural stimulation in proximate groups of ganglion cells. For this purpose, the electrodes or contacts, which are secured to the electrode carrier at spaced locations along its length, should preferably be located as close as possible to the modiolus, i.e., near the radially inner wall 43 of the cochlea, where the spiral ganglion cells 40 to be stimulated are located.

Here, however, a problem has been encountered. The electrode carriers, as already mentioned, are generally manufactured in a straight tapered rod-like form from a resilient polymer or like elastomeric material. By virtue of their being straight or only very slightly curved, the electrode carriers can be smoothly and easily inserted into the scala tympani 36 of the cochlea 32 through the opening in the round window 38 or through a small hole drilled into the basal part of the cochlea. When such an electrode carrier 45 (see FIG. 10) is so inserted into the cochlea 32, it flexibly curves into the spiral form of the scala tympani, but because the electrode carrier is resilient and has a "memory" tending to return it to its straight form, it ends up lying against, and closely following the curvature of, the radially outer wall 44 of the cochlea. As a result, the electrodes 46 on the carrier end up being located in the vicinity of the damaged and non-functional hair cells 39 on the basilar membrane 35 (see FIG. 11) but at a substantial distance (relatively speaking) from the inner wall 43 of the cochlea and hence also relatively far from the ganglion cells 40 in the modiolus, thereby limiting the achievable stimulation of the ganglion cells. In such a case, it is necessary to use stimulation currents which are somewhat higher than is usually deemed desirable, but that in turn leads to an undue overspread of the current and a reduction in the resolution of the stimulus.

In an attempt to overcome these drawbacks, which also have not been overcome by proposals to make the electrode carrier either in a more or less greatly curved form such as a spiral shape (see FIGS. 8 and 9) approximating the curvature of the cochlea and utilizing the memory of the carrier material to return the carrier to that shape after the carrier has been straightened for the purposes of the insertion operation, it was proposed in the aforesaid prior application to make the conventional straight rod-like electrode carrier in the form of two layers. Of these layers, the one which incorporates the electrical contacts or electrodes and their leads (herein designated the inner layer) was described as being made of a biocompatible silicone polymer, e.g., Silastic, which does not expand or swell when exposed to the water in the patient's body fluids, while the other layer (herein designated the outer layer) was described as being suitably adhered to the inner layer at the side of the latter directed away from the contact faces of the electrodes and as being made of a biocompatible silicone polymer (also Silastic) formulated through the addition of finely ground NaCl or polyacrylic acid or the like so as to have the property of expanding (swelling) under the action of the water in the patient's body fluids once the carrier has been inserted into the cochlea. By means of such an arrangement, it was suggested, the outer layer of the electrode carrier would, due to the liquid-generated expansion of the outer layer, be ultimately shifted away from its initial position at the radially outer wall of the cochlea to a second position within the scala tympani where the inner layer has its concavely curved surface, at which the contact faces of the electrodes are located, disposed in engagement with the radially inner wall of the cochlea and thereby in close proximity to the modiolus and the ganglion cells. As a solution to the indicated problem, however, this approach was not perfect because, even at best, achieving a post-implantation precise control of the expansion of the outer layer and of the resultant curvature of the inner layer of the electrode carrier is extremely difficult. Moreover, if an unduly great deviation from the desired curvature were to occur, this might necessitate corrective action by means of additional invasive surgery.

BRIEF DESCRIPTION OF THE INVENTION

It is an object of the present invention, therefore, to provide a system for positioning a stimulating electrode carrier of a cochlear electrode implant assembly optimally in the cochlea of a human ear so as to avoid the drawbacks and disadvantages of known electrode positioning systems and instead to ensure the closest possible proximity of the electrodes to the modiolus and the ganglion cells.

It is another object of the present invention to provide a cochlear electrode positioning system which is characterized by the fact that, although the electrode carrier is initially straight so as to allow for an easy, gentle and controllable insertion thereof into the cochlea, the carrier when inserted is forced by the system to lie closely against and to closely follow the curvature of the radially inner wall of the cochlea, and by the fact that the system enables the curvature of the carrier to be automatically adjusted so as to match that of any size cochlea.

It is a more specific object of the present invention to provide such a cochlear electrode implant assembly which includes, in addition to the flexible rod-like initially straight electrode carrier, an electrode positioning system in the form of a flexible rod-like auxiliary positioning member which is likewise initially straight and is arranged in close juxtaposition to the electrode carrier longitudinally thereof on the side of the electrode carrier directed away from the modiolus-engaging contact faces of the electrodes and which, upon joint insertion thereof with the electrode carrier into the cochlea, assumes an enlarged outward curvature and presses over a major portion of its length against the radially outer wall of the cochlea so as to force the side of the electrode carrier where the contact faces of the electrodes are located as far as possible toward and into close proximity to the modiolus and hence into as close a proximity as possible to the ganglion cells.

It is a further object of the present invention to provide an electrode positioning system as aforesaid with means which serve to lock the assembly consisting of the electrode carrier and the auxiliary positioning member in place within the cochlea-at the end of the insertion stage, thereby to firmly and stably secure the assembly against inadvertent movement in and withdrawal from the cochlea.

Generally speaking, the basic objectives of the present invention are achieved by combining with each initially straight rod-like flexible electrode carrier, to which the requisite series or array of multiple electrodes or contacts (which may be as many as 22 or more in number) is secured in any desired way, an initially straight rod-like flexible auxiliary positioning member which extends along the length of the electrode carrier and has a leading end region and a trailing end region connected to the leading end region and the trailing end region, respectively, of the electrode carrier in a manner to be more fully discussed hereinafter. The electrodes may be in the form of discrete layers or bands secured to and overlying respective full-circumference or part-circumference regions of the rod-shaped electrode carrier (see FIGS. 2–4), or in the form of discrete either planar or dome-shaped layers or other formations, arranged on a carrier of either circular or part-circular or similar cross-section (see FIGS. 5–7), but in all cases located generally at that surface of the electrode carrier which, upon insertion of the carrier into the cochlea, will be concavely curved toward the modiolus. In this assembly, therefore, the auxiliary positioning member is disposed adjacent that surface of the electrode carrier which, upon insertion of the carrier into the cochlea, will be convexly curved away from the modiolus.

In one embodiment of the invention, the leading end region of the positioning member is linked or articulated to the leading end region of the electrode carrier for joint longitudinal movement thereof, while the trailing end region of the positioning member is connected to the trailing end region of the electrode carrier so as to initially permit sliding longitudinal movement of the former relative to the latter. The arrangement is such that when the assembly composed of the electrode carrier and the auxiliary positioning member is initially inserted into the scala tympani, both the electrode carrier and the positioning member are in their starting straight and substantially parallel state, with the medial region of the positioning member between its leading and trailing end regions being separated from (in the sense of being unconnected to) the juxtaposed medial region of the electrode carrier. The inward movement of the assembly is preferably effected by the surgeon gripping and pushing the positioning member with the aid of a suitable insertion tool, and that, by virtue of the interconnected leading end regions of the electrode carrier and the positioning member, causes the electrode carrier to be pulled into the cochlea. When the assembly reaches and enters into the spiral curvature section of the cochlea, however, it is the positioning member (rather than the electrode carrier) which comes with its outer surface up against and rides along the radially outer wall of the cochlea within the scala tympani, while concurrently therewith the electrode carrier comes with a medial section of its electrode-bearing surface up against the proximate initial region of the radially inner or modiolar wall of the cochlea.

Thereupon, the continuing pushing force being exerted by the surgeon on the positioning member causes the trailing end region of the latter to advance somewhat relative to the electrode carrier past the location of the connection between their respective trailing end regions due to the frictional drag exerted by the modiolar wall on the electrode carrier. This results, again by virtue of the interconnections of the leading and trailing end regions of the electrode carrier with the leading and trailing end regions of the positioning member, on the one hand in the medial region of the positioning member between its leading and trailing end regions assuming an outwardly bowed or arched configuration relative to the medial region of the electrode carrier and on the other hand in the leading end region of the positioning member curving away from the outer wall and toward the radially inner wall of the cochlea. The tip of the electrode carrier thus is forced across the width of the scala tympani until the leading end region as well as substantially the entire length of the electrode-bearing surface of the electrode carrier up to the trailing end region thereof is in close hugging contact with the modiolar wall. Upon completion of the insertion, therefore, the electrodes supported by the electrode carrier are then held by the positioning member, due to the latter being outwardly bowed or arched relative to the electrode carrier against the constraint of the radially outer wall of the cochlea, in as close a juxtaposition to the ganglion cells as possible.

Once the electrode carrier has been fully advanced in this manner to the desired final position thereof, the trailing end region of the arched positioning member is locked to the trailing end region of the electrode carrier at the location of their interconnection outside the entrance to the cochlea. The entire assembly will then remain firmly in place, because the arched portion of the positioning member, being unable to straighten out, will remain in full surface contact over a major portion of its length with the radially outer wall of the cochlea, which will stabilize the assembly in the scala tympani and make any inadvertent movement of the electrode carrier in the cochlea and especially a reverse movement thereof out of the cochlea effectively impossible.

More particularly, in the aforesaid embodiment of the present invention, the electrode carrier and the positioning member are both in the form of solid rods and made throughout of respective biocompatible flexible plastic materials. Preferably, the electrode carrier is made of a flexible biocompatible silicone polymer such as Silastic. On the other hand, the positioning member preferably is made from a somewhat harder but still flexible biocompatible polymeric material such as nylon, Teflon or a Teflon-like material (generically known as PTFE or polytetrafluoroethylene), or the like, so as to have the requisite degree of stiffness and tensile strength for enabling it to be used to pull the electrode carrier through the cochlea. Whatever materials the electrode carrier and the positioning member in this embodiment of the present invention are made of must, of course, be so formulated that they will not expand upon being exposed to the water in the patient's body fluids.

The two parts of the assembly in this embodiment of the invention are linked or articulated to one another at their respective leading ends by a ball-and-socket type of joint, of which the ball-part (which may have either a spherical or a non-spherical shape) preferably is supported by the electrode carrier and the correspondingly configured socket-part is formed on the positioning member. In the currently contemplated best mode of implementing the linkage, a small number of wires (preferably 2–4 insulated wires identical to the conductors for the electrodes but not connected to the signal source) are run through the electrode carrier at the time of its manufacture, and these wires terminate outside the tip of the electrode carrier. At the distal ends of these wires a suitable distance from the tip of the electrode carrier, the insulation is stripped off the wires and the so-exposed end regions thereof are melted together to form a ball (or a functionally like solid body), so that the latter is effectively supported by the electrode carrier through the intermediary of the wires. Correspondingly, the leading end region of the positioning member is provided with a frontwardly open axial slit disposed in the common axial plane of the assembly and dimensioned, both lengthwise and widthwise, to accommodate the portion of the ball-supporting bundle of wires between the ball and the tip of the electrode carrier. The positioning member is also provided at the rearwardmost end of the slit on the outer surface of the positioning member with an enlarged suitably configured open-topped recess or depression facing away from the electrode carrier to constitute the socket for receiving the ball.

The currently preferred means for locking the assembly according to this embodiment of the invention in place is a fitting having a body in the form of a generally S-shaped structure made of a strip of titanium or like biocompatible metal and defining in its opposite end regions (the loops of the "S") a pair of substantially parallel passageways extending through the fitting parallel to its axis and separated from each other by a medial axial partition (the center web of the "S"), the passageways being intended, one for accommodating the electrode carrier and the other for accommodating the positioning member. The portion of the body of the fitting which defines the passageway through which the electrode carrier extends is fixed to the trailing end region of the electrode carrier, e.g., by being crimped thereonto, somewhat rearwardly of the trailing end of the array of electrodes, while the portion of the body of the fitting which defines the passageway through which the positioning member extends is provided with wedge-like means arranged to permit forward movement but prevent reverse movement of the positioning member through that passageway. The wedge-like means preferably has the form of a short strip of metal which is affixed at one end edge thereof to the medial partition of the fitting and extends from its attachment location along the proximate face of the partition in the direction of forward movement of the positioning member, the wedging strip terminating at an opposite relatively sharp free end edge thereof and being oriented at an inclination relative to the partition and toward the axis of the passageway through which the positioning member extends.

It will be understood, therefore, that the positioning member can slide freely past the free end edge of the wedging strip when moving in the forward direction during the insertion stage, i.e., while the pushing force is being exerted on the positioning member. On the other hand, upon completion of the insertion stage (or, for that matter, at any time during the insertion stage), if the pushing force is relaxed and the positioning member starts to move in the reverse direction, the free end edge of the wedging strip will immediately bite, i.e., penetrate slightly on a bias, into the positioning member and will create a pawl-like wedging effect, thereby to inhibit any further reverse movement of the positioning member and to lock the entire implant assembly in place.

In another embodiment of the invention, the positioning member again has a straight rod-like configuration in the starting (pre-insertion) state of the assembly and is located lengthwise of and in close parallel relation to the electrode carrier. In this case, however, the positioning member is not a solid rod but rather is constituted by an elastic axially compressed tube of Silastic or like biocompatible plastic material, this tube even in its compressed state being longer than the array of electrodes on the electrode carrier. A platinum wire (this is preferred, although any type of tension member of a biocompatible material other than platinum or platinum alloy, even of a non-metallic material, can be used as long as it has the requisite physical properties, and the term "wire" should be so interpreted) extends axially slidably through the tube to impart stiffness to the tube. The leading end region of the wire, which protrudes from the leading end of the compressed tube, has a reverse bend formed therein, defining a hook-like portion the free end of which is secured to, e.g., molded into, the tip of the electrode carrier, with the bend in the wire constituting a hinge portion about which the positioning member can move angularly (pivotally) relative to the electrode carrier in the common axial plane of the assembly. The compressed tube has its leading end region located adjacent the leading end region of the electrode carrier and has its trailing end region fixedly secured or anchored to the electrode carrier somewhat rearwardly of the trailing end of the electrode array. The trailing end region of the wire extends somewhat beyond the trailing end region of the compressed tube and is initially straight and held fast, e.g., clamped, to the electrode carrier at that location. In this way, the wire keeps the compressed tube straight as well and prevents any premature movement of the positioning member relative to the electrode carrier.

As before, the initial insertion of the assembly into the cochlea takes place while both the positioning member and the electrode carrier are in their straight state, with the surgeon in this case exerting the needed pushing force on the electrode carrier. During the entire insertion operation, the trailing end of the wire remains clamped in place on the electrode carrier, and thus the wire is constrained against movement relative to the carrier, thereby ensuring that the compressed tube also remains straight. Thus, when the assembly consisting of the positioning member and the electrode carrier enters the spirally curved section of the cochlea, both the positioning member and the electrode carrier become correspondingly curved, with the positioning member over substantially its entire length being in contact with the radially outer wall of the cochlea, and with the electrode carrier closely following the curvature of the positioning member and consequently disposing the contact faces of the electrodes out of the desired degree of proximity to the modiolar wall and the ganglion cells.

Once the insertion operation has been carried out to the fullest extent possible, however, the trailing end of the wire is unclamped from the electrode carrier. This releases the constraint exerted by the wire on the compressed tube and permits the tube to expand longitudinally so as to assume, by virtue of the fact that the leading and trailing end regions of the tube are effectively held stationary on the electrode carrier and that an additional portion of the new released wire is drawn into the tube, an outwardly arched or bowed configuration relative to the electrode carrier. As a result, the expanding tube acts in the manner of a spring and, aided by the stiffening effect of the wire confined within the tube, exerts an outward force on the radially outer wall of the cochlea. By virtue of the interconnection of the leading end regions of the positioning member and the electrode carrier, therefore, the arching of the positioning member forces the tip of the electrode carrier across the width of the scala tympani until it comes into contact with the radially inner wall of the cochlea and concomitantly therewith causes the electrode-bearing surface of the electrode carrier to come along its entire length into close hugging contact with the modiolar wall. It will furthermore be understood, in this regard, that when, in the described final position of the assembly, the trailing end region of the wire is again fastened, i.e., reclamped, to the electrode carrier, the arched positioning member constituted by the tube and the wire which is enclosed therein constitutes the means for locking the assembly in place by virtue of the fact that, in the absence of a pulling force exerted on the wire, the arched positioning member is effectively precluded from returning to its original straight state, so that any instability or inadvertent movement of the assembly in the cochlea or reversely out of the cochlea is effectively inhibited.

In accordance with yet another embodiment of the invention, the assembly initially consists of a straight rod-like electrode carrier which is made of Silastic silicone plastic material that is inert to and does not expand under the action of the water in the patient's body fluids, and a straight rod-like positioning member which is likewise made of Silastic silicone plastic material but one that is formulated to be responsive to and to expand or swell under the action of the water in the patient's body fluids. As disclosed in the aforesaid application Ser. No. 211,269, the Silastic silicone polymer may be rendered water-swellable by mixing it with predetermined amounts of finely ground NaCl, polyacrylic acid, or like substances which in effect draw in water when exposed to the body fluids. The electrode carrier and the positioning member initially are effectively equal in length and are molded or otherwise secured, e.g., bonded, to each other at their respective leading and trailing end regions, and between those locations they are disposed substantially parallel to and separated from (unconnected to) each other.

In use, this assembly is initially inserted into the scala tympani, as before, while still in its straight state, and the insertion is then continued by the surgeon pushing the assembly to advance along the spirally curved section of the cochlea. During this stage of the operation, the positioning member and the electrode carrier both become correspondingly curved, with the positioning member over substantially its entire length being in contact with the radially outer wall of the cochlea, and with the electrode carrier closely following the curvature of the positioning member and disposing the contact faces of the electrodes out of the desired close proximity to the modiolus. Once the insertion operation has been carried out to the fullest possible extent, however, no further action by the surgeon to shift the electrode carrier to its desired position is required. Rather, the subsequent swelling of the positioning member over a period of time as it is exposed to the patient's body fluids will cause the positioning member to assume, by virtue of its fixed connection at both ends to the electrode carrier, an outwardly bowed or arched configuration relative to the electrode carrier so as to exert an outward force against the radially outer wall of the cochlea. As a result of the expansion of the positioning member, therefore, the electrode carrier is forced by the positioning member, due to the interconnection between the leading and trailing end regions of the latter with the leading and trailing end regions of the electrode carrier, toward and against the radially inner wall of the cochlea, which causes the electrode-bearing surface of the electrode carrier to come along its entire length into close hugging contact with the modiolar wall. Here too, the arched positioning member, which in the stated environment is precluded from returning to its original straight state, serves as the means for locking the assembly in place and for preventing any instability of the assembly in or reverse movement thereof out of the cochlea.

The principal advantage of the positioning system according to all of the embodiments of the present invention is that the presence of the positioning member alongside the electrode carrier, with their opposite end regions connected to and with their medial regions separated from each other, ensures that the electrode-bearing face of the electrode carrier ends up in close hugging contact with the modiolus so as to juxtapose the electrode contact faces as close to the ganglion cells as possible. A related advantage is that the curvature of the electrode carrier is automatically adjusted to that of the cochlea irrespective of the size of the cochlea, so that a pre-insertion adaptation of the system to any particular patient's cochlea is not required.

BRIEF DESCRIPTION OF THE DRAWINGS

The foregoing and other objects, characteristics and advantages of the present invention will be more clearly understood from the following detailed description thereof when read in conjunction with the accompanying drawings, which are basically schematic or diagrammatic in nature and should be viewed as such, in which:

FIGS. 1A and 1B, which have already been discussed previously herein, are diagrammatic interior views, not necessarily drawn to scale, of those portions of the human ear, including the cochlea, the structural and functional characteristics of which are relevant to an understanding of the present invention, with FIG. 1A generally showing the overall structure of the ear partly in elevation and partly in longitudinal section, while FIG. 1B is a greatly enlarged cross-sectional view, taken along the line 1B—1B in FIG. 1A, which generally illustrates the structure of the cochlea;

FIGS. 2–9, which have also been discussed above, are schematic illustrations of various types of known electrode carriers for cochlear implant systems, with FIGS. 2, 3, 5, 6 and 8 being fragmentary elevational views, partly in section, of the electrode carriers, while FIGS. 4, 7 and 9 are cross-sectional views taken along the lines 4—4, 7—7 and 9—9 in FIGS. 3, 6 and 8, respectively;

FIG. 12 is a fragmentary longitudinal sectional view, partly in elevation, of a cochlear electrode carrier/positioning member assembly according to one embodiment of the present invention in the pre-insertion state of the assembly and illustrates one type of joint for interconnecting the leading end regions of the electrode carrier and the positioning member and a wedging type of fitting for interconnecting the trailing end regions of the electrode carrier and the positioning member for one-directional movement of the latter relative to the former;

FIG. 13 is a view similar to FIG. 12 but illustrates the assembly in its post-insertion state and shows the fitting as wedging the positioning member against reverse movement for locking the assembly in place in the cochlea;

FIG. 14 is a perspective illustration of the wedge-type fitting shown in FIGS. 12 and 13;

FIG. 15 is a perspective illustration of a slightly modified version of the fitting shown in FIG. 14;

DETAILED DESCRIPTION OF THE INVENTION

Figure 1A:
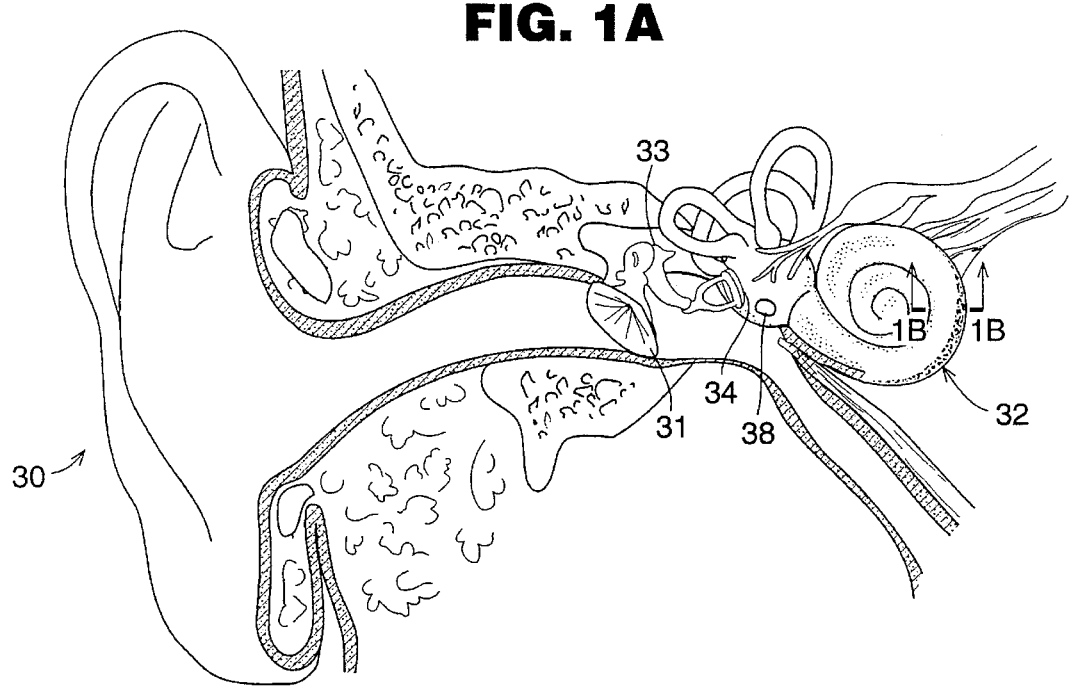
Figure 1B:
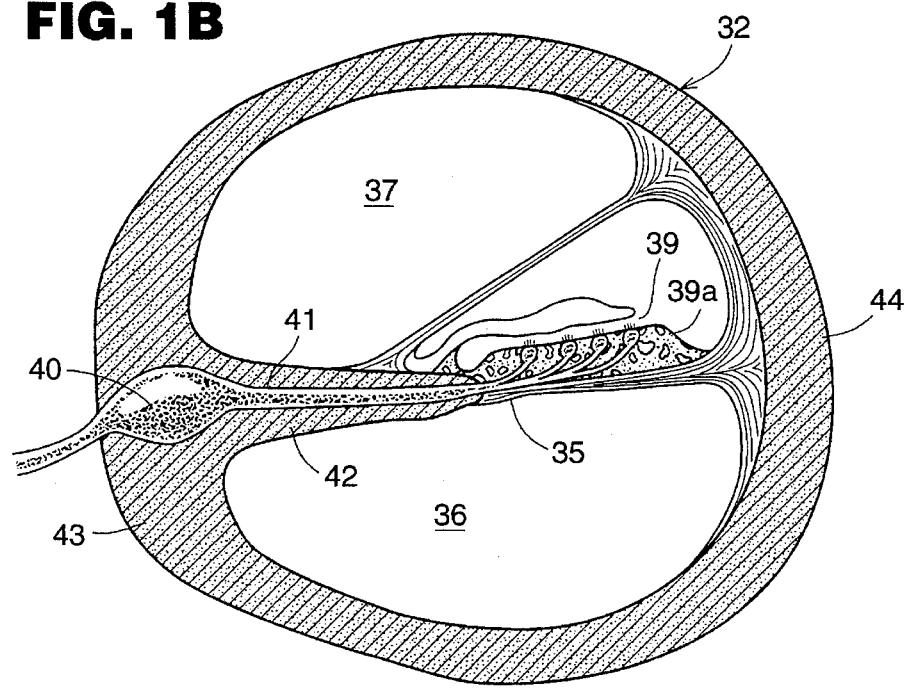
Figure 2:
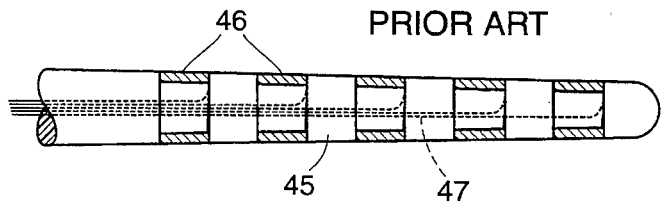
Figure 3:
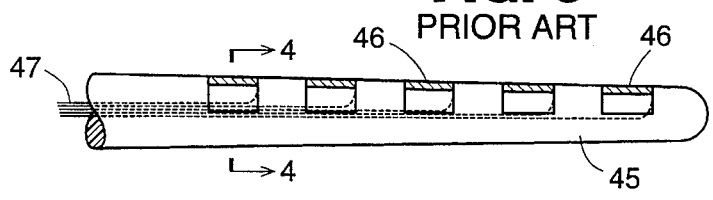
Figure 4:
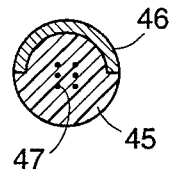
Figure 5:
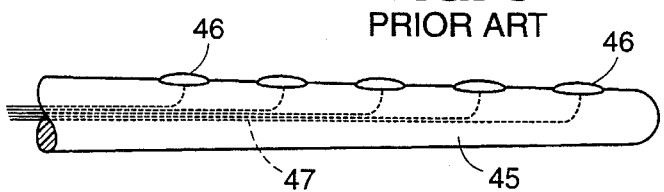
Figure 6:
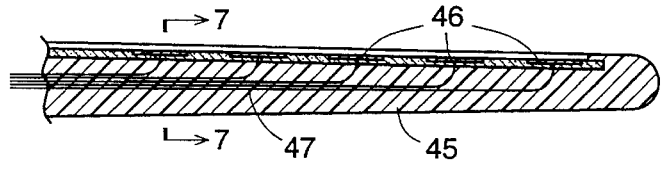
Figure 7:
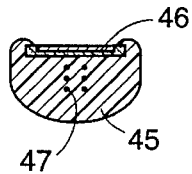
Figure 8:
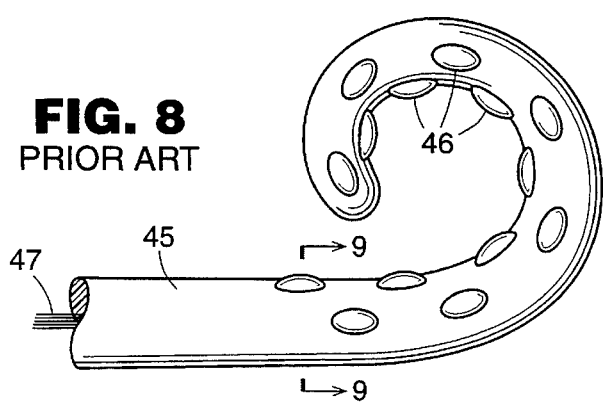
Figure 9:
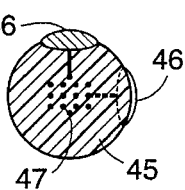

Referring now to the drawings in greater detail, FIGS. 12 and 13 show a cochlear electrode implant assembly 50 which, in accordance with a first embodiment of the present invention, includes an electrode carrier 51 of a per se known type and a novel associated auxiliary positioning member 52, together with means 53 for connecting the leading end region 51a of the electrode carrier to the leading end region 52a of the positioning member and with means 54 for connecting the trailing end region 51b of the electrode carrier to the trailing end region 52b of the positioning member. Thus, on the one hand the electrode carrier 51 is shown, merely by way of example, as having the structure of the electrode carrier of FIGS. 3 and 4, i.e., as being a straight flexible solid rod of circular cross-section, which is made of Silastic silicone plastic or an equivalent biocompatible material, which at one side region thereof and in a medial region 51c between the leading and trailing end regions 51a and 51b bears an array of longitudinally spaced electrode elements 55 in the form of part-cylindrical bands or layers of a biocompatible metal such platinum or platinum alloy, and which further has a series of insulated electrical conductors 56 made of like biocompatible metals and embedded in its interior for conducting stimuli in the form of electrical sound-representing signals or impulses to the various electrode elements. (It will be understood, of course, that the electrode carrier and its electrode elements may just as well have any of the other configurations thereof shown in FIGS. 2 and 5–9, although not the precurved spiral shape shown in FIG. 8.)

On the other hand, the auxiliary positioning member 52 in this embodiment of the invention is a flexible solid rod of preferably circular cross-section, which is shown as being somewhat thinner than the electrode carrier 51 (although this is not an essential or indispensable condition). The positioning member, which initially is also generally straight, is juxtaposed to the side region of the electrode carrier opposite to the one where the contact faces of the electrode elements 55 are exposed and extends lengthwise of and along the electrode carrier so as to have its leading and trailing end regions 52a and 52b adjacent, respectively, to the leading and trailing end regions 51a and 51b of the electrode carrier and so as to have its medial region 52c between the leading and trailing end regions 52a and 52b separated from, i.e., unconnected to, the medial region 51c of the electrode carrier. The positioning member is likewise made of a biocompatible material which may be Silastic silicone plastic but, for purposes of enhanced stiffness and tensile strength, is preferably a harder material such as nylon, Teflon or a Teflon-like material (polytetrafluoroethylene), or the like.

The connection 53 between the leading end region 52a of the positioning member and the leading end region 51a of the electrode carrier in the embodiment of FIGS. 12 and 13 is effected by means of a ball-and-socket joint which, in the illustrated arrangement, includes a ball element supported by the electrode carrier and a socket portion located on the positioning member. More particularly, the electrode carrier 51 at the time of its manufacture is provided in its interior with a few, preferably from 2 to 4, additional insulated wires 56a which are physically identical to and extend longitudinally through the electrode carrier like the wires 56 but are not connected to the source of the electrical stimuli. The bundled wires 56a protrude a short distance forwardly beyond the tip of the electrode carrier and at their distal end regions are melted and fused to each other into the form of a ball 53a. Correspondingly, the positioning member 52 is provided at its tip with a frontwardly open and rearwardly extending axial slit 53b just wide enough to accommodate the thickness of the bundle of wires 56a which support the ball element 53a, and at its side facing away from the electrode carrier the positioning member is provided with an appropriately configured and dimensioned open-topped arcuate recess or depression 53c which symmetrically bridges the rearwardmost end of the slit. During the assembly operation, therefore, it is merely necessary to slip the projecting section of the bundle of wires into the slit and to slide the ball over the top surface of the positioning member until it is received in the recess.

It should be understood, in this regard, that although as a general proposition the ball element 53a of the ball-and-socket joint 53 will preferably be a ball having a spherical or hemispherical shape while the recess 53c constituting the socket portion of the joint will have a depth, curvature and overall contours enabling the ball to be properly and securely received and seated therein, other forms thereof could also serve the functional purposes of the joint; for example, the "ball element" could be cylindrical or rod-like in shape adapted to be received and seated in a correspondingly shaped groove or notch. The terms "ball element" and "ball-and-socket joint" thus are intended to be, and should be, interpreted in their broadest possible sense.

The connection 54 between the trailing end region 51b of the electrode carrier and the trailing end region 52b of the positioning member in the embodiment of FIGS. 12 and 13 is effected by means of a metallic double tubular fitting 57 which is made of titanium strip and has a body in the form of a generally S-shaped structure (see FIG. 14). The essentially tubular loops 57a and 57b of the "S" define a pair of substantially parallel passageways 57c and 57d which extend through the fitting along respective axes parallel to the axis of the fitting and are separated from each other by an interior partition 57e constituted by the center web of the "S." Within the passageway 57d there is provided, in accordance with one version of the fitting 57 contemplated by the present invention, an additional strip 57f of titanium which along one end edge thereof is spot-welded to the partition 57e at 57g and extends forwardly from that location through the passageway 57d at an inclination toward the axis of that passageway. The distal end edge 57h of the strip 57f is relatively sharp for a purpose to be more fully explained presently.

The passageway 57c is initially dimensioned to freely slidably accommodate the electrode carrier 51 for insertion thereof into that passageway, with the portion of the titanium strip which constitutes the loop 57a being sufficiently flexible and strong to permit it to be crimped onto and thereby permanently affixed to the electrode carrier. The passageway 57d, on the other hand, is dimensioned so that, as is clear from FIG. 12, at all times a substantially free and unimpeded sliding movement of the positioning member 52 relative to the fitting 57 and the electrode carrier 51 fixed thereto can take place only in the forward direction through the gap defined in the passageway 57d between the bottom of the loop 57b and the distal end edge 57h of the inclined strip 57f and so that, as is clear from FIG. 13, no movement of the positioning member relative to the fitting in the reverse direction can take place because immediately upon commencement of such a movement the angled strip 57f will exert a pawl-like wedging action on the positioning member by virtue of the sharp end edge 57h of the strip biting into the proximate side region of the positioning member. That wedging action will be further assisted by the fitting, and especially so when the positioning member has assumed its outwardly bowed or arched configuration (only the beginning portion of which is shown in FIG. 13), because concurrently with the edge 57h biting into one side region of the positioning member, the equally sharp inner bottom edge 57i of the loop 57b will bite into the opposite side region of the positioning member.

Referring now to FIG. 15, the S-shaped or double tubular fitting 57' there shown is functionally fully and structurally almost fully identical to the fitting 57. The only difference between them is that the fitting 57' is totally a one-piece rather than a two-piece structure. This is accomplished by utilizing a starting titanium strip which in its original flat state (not shown but readily visualizable from FIG. 15) is essentially T-shaped in outline, with the wedging strip 57f being formed as a part of the overall shaping operation by bending the laterally projecting extension (the leg of the "T") of the middle portion of the original titanium strip which ultimately constitutes the partition 57e' over at 57g' into the confines of the loop 57b' and the passageway 57d' defined therein.

Figure 17:
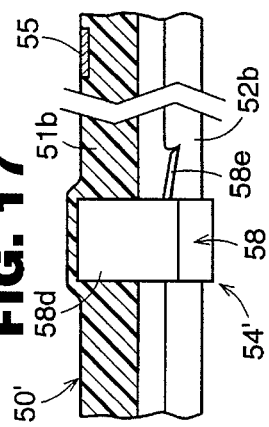
FIG. 17 is a fragmentary side elevational view, partly in section, of a cochlear electrode implant assembly utilizing the wedge-type fitting of FIG. 16 and shows the fitting as having its electrode carrier-accommodating section molded to the electrode carrier and as having its positioning member-accommodating section in the wedging state thereof.
Figure 16:
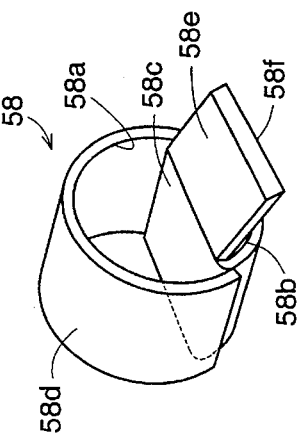
FIG. 16 is a perspective illustration of a different form of wedge-type fitting which has a generally tubular structure and may be used with the cochlear electrode implant assembly of FIGS. 12 and 13.

The provision and use of a somewhat different form of wedging-type fitting 58 for effecting the connection 54' between the trailing end regions 51b of the electrode carrier 51 and the positioning member 52 are illustrated in FIGS. 16 and 17. In the electrode carrier/positioning member assembly 50' according to this embodiment of the present invention, the fitting 58 is a tubular structure which is constituted by a strip of titanium or like biocompatible sheet metal arcuately bent into the form of a cage-like body defining two axially extending substantially parallel passageways 58a and 58b separated from each other by an interior transverse partition 58c. As in the case of the fittings 57 and 57', the passageway 58a accommodates the electrode carrier 51 and the passageway 58b accommodates the positioning member 52. The portion of the body of the fitting 58 through which the electrode carrier extends here is shown as being fixed to the latter by having a section 58d of the cage-forming strip molded into the electrode carrier somewhat rearwardly of the array of electrodes 55 (see FIG. 17), although the affixation could just as well be effected by crimping, while the portion of the body of the fitting through which the positioning member extends is dimensioned to permit longitudinal sliding movement of the positioning member. For the purposes of achieving the desired one-way movement of the positioning member relative to the fitting 58, the latter is provided with a pawl-like element 58e which extends from the partition 58c in the forward direction, is inclined at a small angle, on the order of about 10°–15° or so, relative to the axis of the fitting and in a direction toward the axis of the passageway 58b, and terminates in a forwardly directed moderately sharp transverse distal edge 58f. The positioning member can, therefore, slide relatively freely past the pawl-like element 58e in the forward direction but, because of the pawl-like wedging action of the element 58e as it bites into the positioning member (see FIG. 17), cannot move relative to the fitting in the reverse direction.

Figure 18:
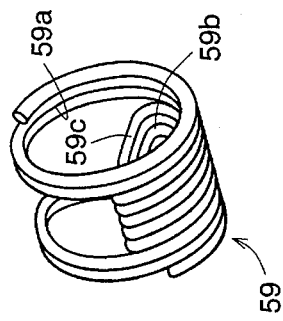
FIG. 18 is a perspective illustration of yet another form of tubular fitting which may be used with the cochlear electrode implant assembly of FIGS. 12 and 13 but permits bidirectional movement of the positioning member and therefore requires a crimping of a portion of the fitting onto the positioning member to lock the latter against reverse movement.
Figure 19:
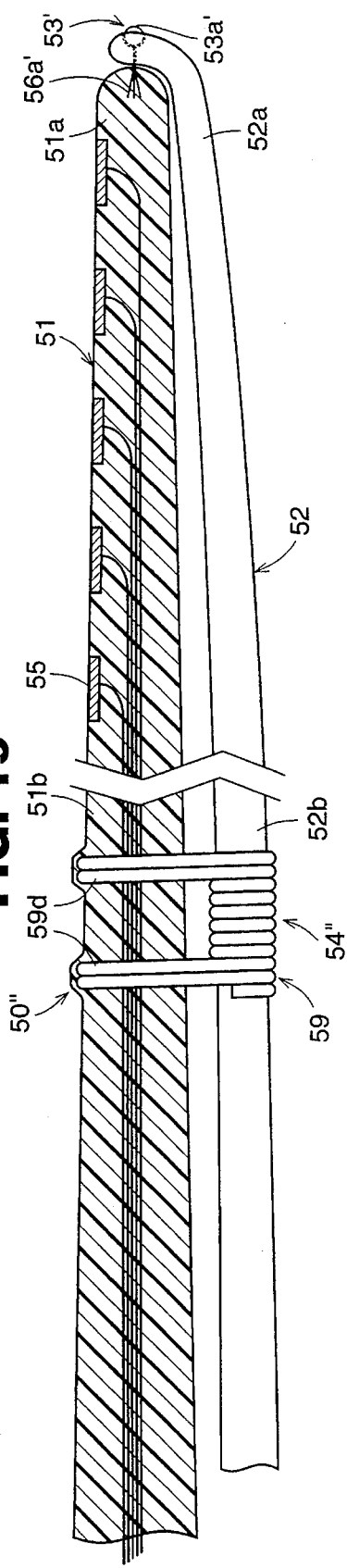
FIG. 19 is a fragmentary side elevational view, partly in section, of a cochlear electrode implant assembly utilizing the crimp-type fitting of FIG. 18 and shows the fitting as having its electrode carrier-accommodating section molded to the electrode carrier.

Yet another type of fitting 59 for effecting the connection 54" between the trailing end regions 51a and 52a of the electrode carrier 51 and the positioning member 52 is illustrated in FIGS. 18 and 19. In the assembly 50" according to this embodiment of the present invention, the fitting 59 is constituted by a length of wire of titanium or a like biocompatible metal spirally wound into the form of cage-like body defining two axially extending substantially parallel passageways 59a and 59b separated from each other by an interior transverse partition 59c. The passageway 59a accommodates the electrode carrier 51, and the passageway 59b accommodates the positioning member 52. In the illustrated assembly 50", the portion of the body of the fitting 59 through which the electrode carrier 51 extends is shown as being fixed to the latter by, e.g., having respective portions 59d of the cage-forming wire molded into the electrode carrier somewhat rearwardly of the trailing end of the array of electrodes 55, while that portion of the body of the fitting through which the positioning member 52 extends accommodates the positioning member for longitudinal sliding movement through the passageway 59b in both the forward and the reverse directions. For the purposes of ultimately locking the positioning member in this assembly against movement relative to the electrode carrier and the fitting in the reverse direction, the fitting must be sufficiently deformable so as to enable it to be crimped onto the positioning member (the locking action will, of course, be inherently effective against movement of the positioning member relative to the electrode carrier in either direction).

The electrode carrier/positioning member assembly 50" according to the embodiment of the present invention shown in FIG. 19 also includes, for effecting the desired linkage or articulated connection between the leading end regions 51a and 52a of the electrode carrier 51 and the positioning member 52, a ball-and-socket joint 53' which is a slightly modified version of the ball-and-socket joint 53 shown in FIG. 12. In the joint 53' the means for attaching the ball element 53a' to the electrode carrier comprises, in lieu of a bundle of wires, a flexible web or strand (or a bundle of strands) 56a' of Dacron polyester or a comparable biocompatible fibrous material, the web or strand being molded at one end thereof into the leading end region 51a of the electrode carrier and at its other end into the ball element. It should be understood, however, that of the two ball-and-socket joints herein disclosed, the joint 53 is preferred and currently constitutes what is deemed to be the best mode of effecting the linkage between the leading end regions of the electrode carrier and the positioning member in the assemblies 50, 50' and 50".

Figure 20:
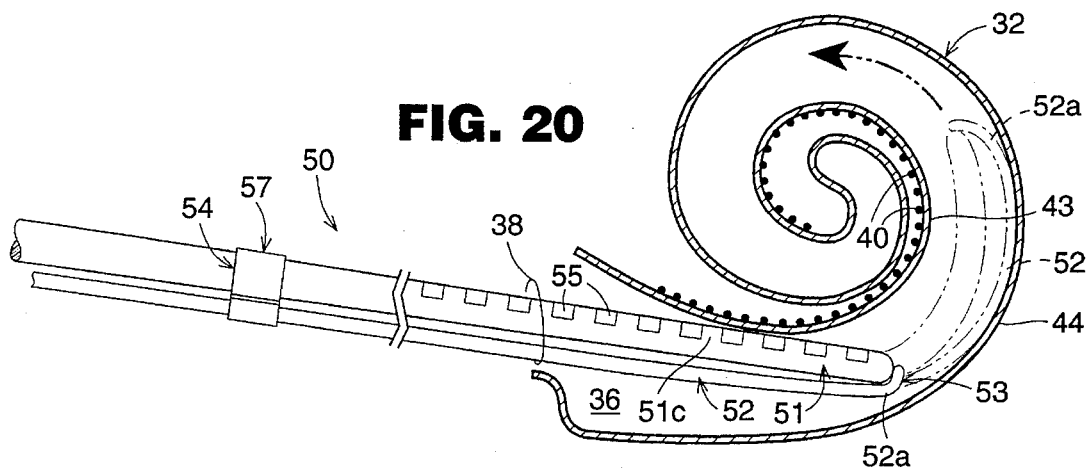
FIGS. 20 and 21 are schematic illustrations in longitudinal section, respectively, of the initial and final stages of the insertion of a cochlear electrode carrier and positioning member assembly according to the embodiment of the invention shown in FIGS. 12 and 13 into the cochlea of a human ear, with FIG. 21 showing the satisfactory final locked position of the electrode carrier.

Referring now to FIG. 20, in the initial phase of the implantation of the electrode carrier/positioning member assembly 50 (or 50' or 50") into the cochlea 32, the leading end region of the assembly in its straight state is inserted into the scala tympani 36 through the round window 38, with the side region of the electrode carrier 51 where the contact faces of the electrodes 55 are exposed being directed toward the radially inner wall 43 of the cochlea and with the positioning member 52 lying at and along the side region of the electrode carrier which is directed toward the radially outer wall 44 of the cochlea. This phase of the insertion movement, which is effected by the surgeon pushing the positioning member longitudinally ahead with the aid of a suitable tool (not shown) and results in the electrode carrier being effectively pulled along by the positioning member due to the presence of the linkage 53 (not shown in FIGS. 20 and 21), continues until the bend in the leading end region 52a of the positioning member 52 comes into contact with the radially outer wall 44 of the cochlea, at which time a portion of the medial electrode-bearing region 51c of the electrode carrier is in contact with a portion of the radially inner wall 43 of the cochlea.

As the pushing force then continues to be exerted on the positioning member 52 by the surgeon, the assembly enters the spirally curved section of the cochlea and begins to adopt the curvature of the cochlea, with the positioning member continuing to glide along the radially outer wall 44 of the cochlea as indicated in phantom outline in FIG. 20. At the same time, however, the frictional drag being exerted by the radially inner wall 43 on the electrode carrier tends to retard the movement of the electrode carrier somewhat relative to the movement of the positioning member. Thus, the continuing pushing force that is exerted by the surgeon on the positioning member causes the trailing end region of the latter to advance somewhat relative to the electrode carrier past the location of the fitting 57 (or 57', 58 or 59). As a result, by virtue of the connections 53 and 54 (or 53' and 54' or 54") between the leading and trailing end regions of the electrode carrier and, respectively, the leading and trailing end regions of the positioning member and by virtue of the separation between the medial regions of the electrode carrier and the positioning member, the leading end region of the positioning member begins curving away from the outer wall 44 of the cochlea, as also shown in phantom outline in FIG. 20. With the positioning member exerting an outwardly directed force on the radially outer wall of the cochlea, the leading end region of the electrode carrier is forced across the width of the scala tympani as the medial region of the positioning member between its leading end region and the part of its trailing end region then extending through the fitting 57 (or 57', 58 or 59) begins to assume an outwardly bowed or arched configuration relative to the medial region of the electrode carrier.

Figure 10:
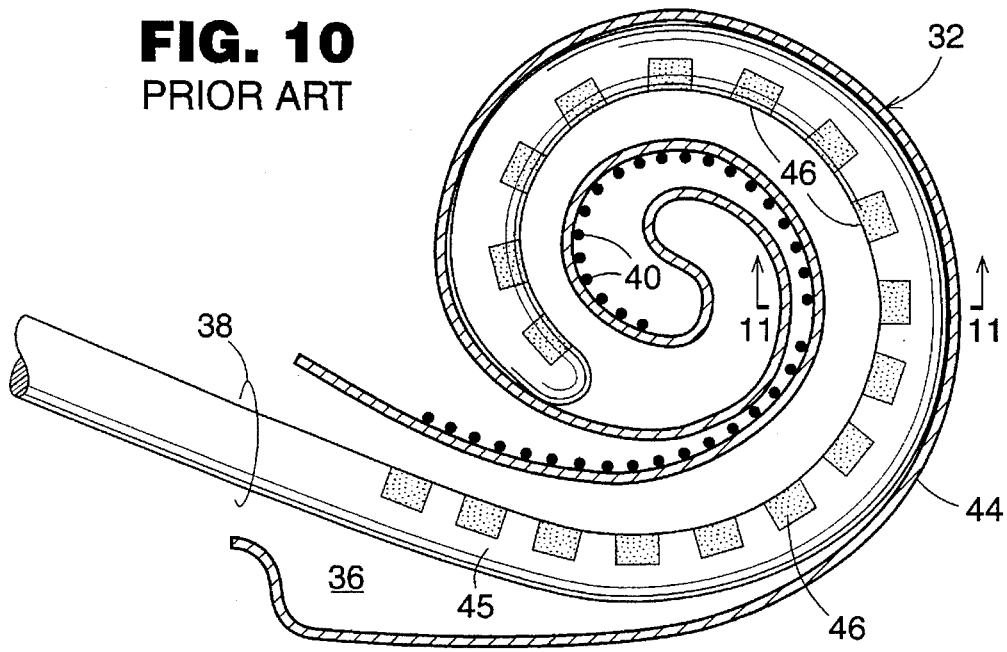
FIGS. 10 and 11, which have already been discussed above, schematically illustrate the cochlea of a human ear having one of the known electrode carriers inserted thereinto and show the unsatisfactory final position of the electrode carrier and its array of electrodes in the cochlea, with FIG. 11 being a greatly enlarged cross-sectional view taken along the line 11—11 in FIG. 10.
Figure 11:
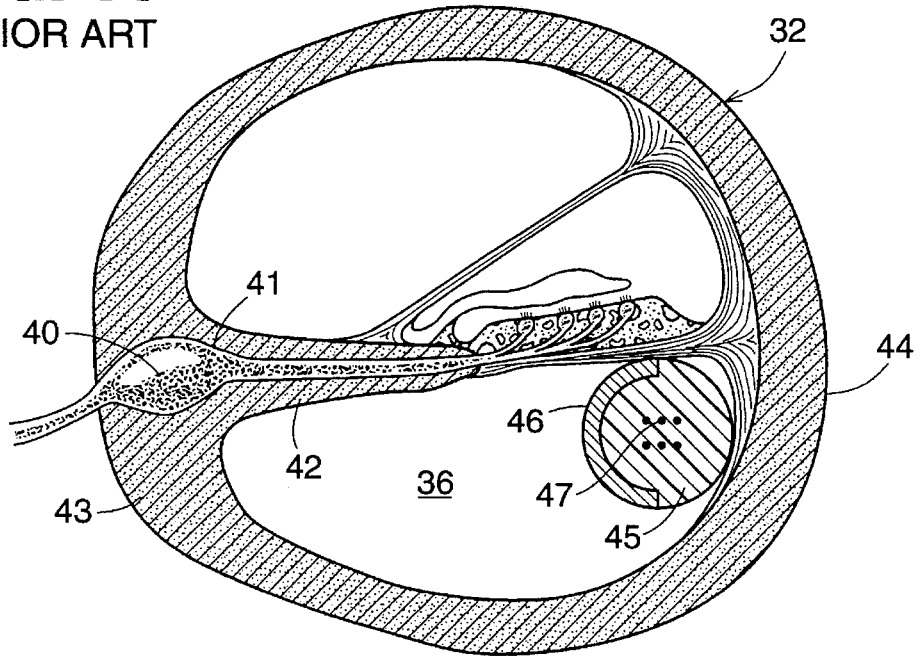
Figure 22:
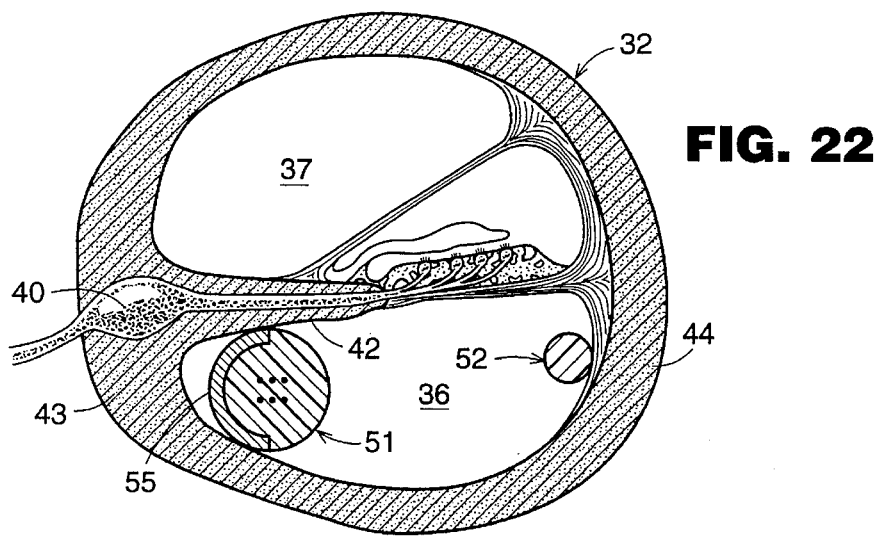
FIG. 22 is a greatly enlarged cross-sectional view taken along the line 22—22 in FIG. 21.
Figure 21:
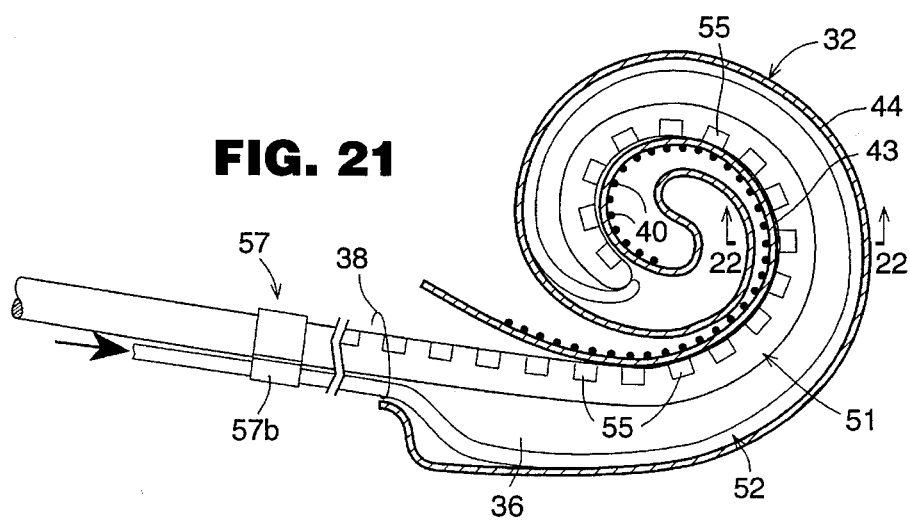

By the time the assembly has reached the end of the spiral section of the cochlea, therefore, as is indicated diagrammatically in FIG. 21, the forces exerted by the positioning member through its leading and trailing end regions on the corresponding end regions of the electrode carrier ensure that not only the leading and trailing end regions of the electrode carrier but also its medial region over substantially the entire length of its electrode-bearing surface are shifted across the scala tympani into close hugging contact with the radially inner wall 43 of the cochlea, thereby disposing the electrodes 55 in as close a juxtaposition to the modiolus and the ganglion cells 40 as possible (see also FIG. 22) and not in the vicinity of the damaged hair cells (which is the situation illustrated in FIGS. 10 and 11). The positioning member thus not only achieves the desired disposition of the electrodes in proximity to the ganglion cells but also serves as the means for holding them in that disposition by virtue of the fact that the outward force exerted by the positioning member on the radially outer wall 44 of the cochlea ensures that the electrode carrier is continuously forced and held against the radially inner wall 43 of the cochlea.

Once the electrode carrier/positioning member assembly has been fully advanced into the cochlea to the desired final position of the electrode carrier, the fitting 57 (or 57' or 58), which is then located just outside the entrance to the cochlea, becomes a means for locking the entire assembly in place within the cochlea. This is achieved automatically and without the surgeon having to perform any positive act toward that end. As previously mentioned, the fitting 57 (or 57' or 58) effectively provides for a one-directional forward movement of the positioning member therethrough. Thus, in this case the positioning member can move substantially freely past the edge 57h (or 57h' or 58f) of the wedging element 57f (or 57f' or 58e) in the forward direction during the insertion stage, i.e., while the pushing force is being exerted on the positioning member by the surgeon. When the insertion stage has been completed, however, and the pushing force is relaxed, any reverse movement of the then bowed or arched positioning member is effectively precluded because as soon as such a reverse movement starts, the wedging element immediately bites into the positioning member (in the case of the fittings 57 and 57' assisted by the likewise functioning edges 57i and 57i'), thereby inhibiting any reverse movement thereof. Thus, since the medial region of the positioning member cannot straighten out and must remain in full surface contact over the major portion of its length with the radially outer wall of the cochlea, any instability or inadvertent movement of the assembly and especially of the electrode carrier in the cochlea is rendered effectively impossible.

In the case of the assembly 50", on the other hand, the same result is achieved except that the surgeon must perform a positive act in order to effect the locking action when the insertion of the assembly has been completed. Thus, the surgeon must crimp the portion of the body of the fitting 59 through which the positioning member extends against the latter so as to prevent any further movement of the positioning member relative to the fitting and the electrode carrier in either direction. In this way, the assembly is constrained to remain firmly in its desired implanted position, because the medial region of the positioning member, being unable to straighten out, must remain in its arched state and hence in full surface contact over the major portion of its length with the radially outer wall of the cochlea. As a result, any instability or inadvertent movement of the electrode carrier in the cochlea, and especially a reverse movement thereof out of the cochlea, is rendered effectively impossible.

Figure 23:
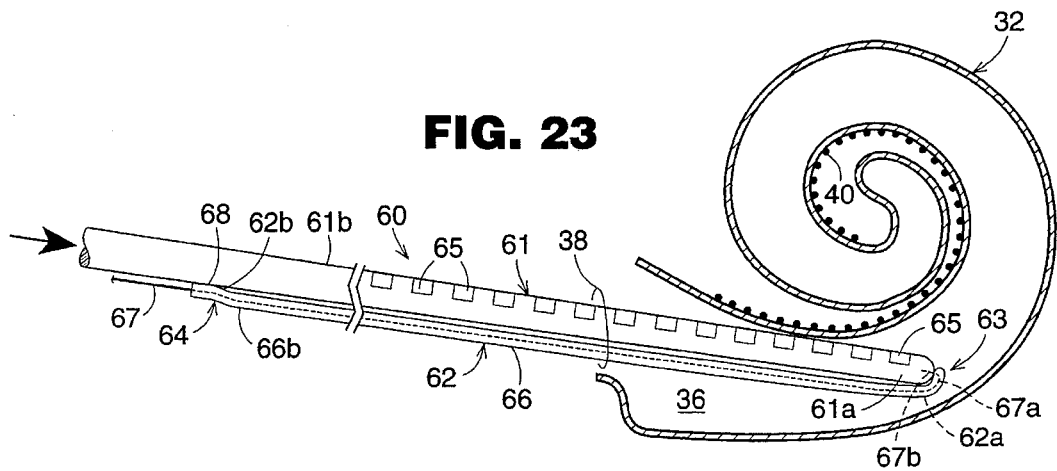
FIGS. 23, 24 and 25 are schematic illustrations in longitudinal section, respectively, of the initial, intermediate and final stages of the insertion of a cochlear electrode carrier and positioning member assembly according to a second embodiment of the present invention into the cochlea of a human ear, with FIG. 25 showing the satisfactory final locked position of the electrode carrier.
Figure 24:
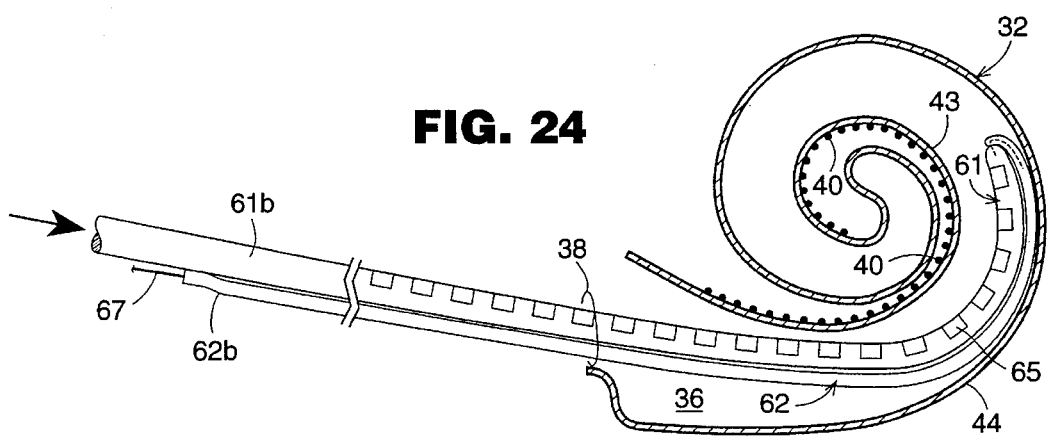
Figure 25:
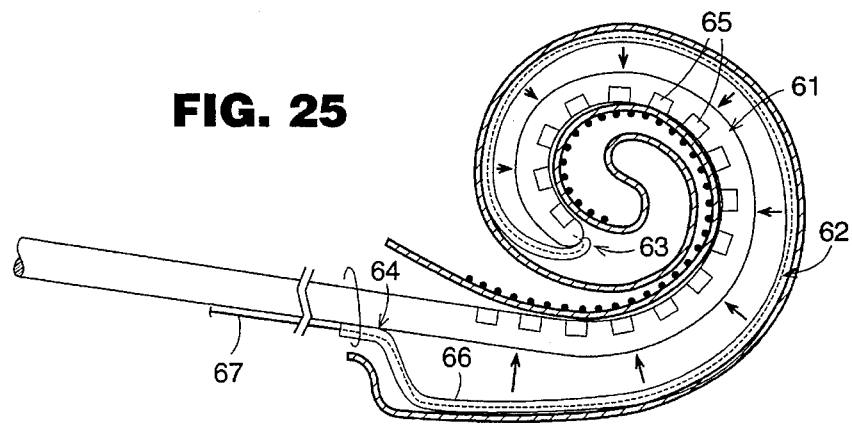

Referring now to FIGS. 23–25, in the embodiment of the invention there shown the electrode carrier/positioning member assembly 60 includes an electrode carrier 61 and a positioning member 62 which are arranged alongside one another and include means 63 connecting the leading end region of the electrode carrier to the leading end region of the positioning member and means 64 connecting the trailing end region of the positioning member to the trailing end region of the electrode carrier somewhat rearwardly of the trailing end of the array of electrodes 65 on the electrode carrier. Whereas in the embodiment of FIGS. 20–22, however, both the electrode carrier and the positioning member are solid rods of the appropriate biocompatible plastic material, as shown in FIGS. 12–13, 17 and 19, in the embodiment of FIGS. 23–25 only the electrode carrier 61 is such a solid rod. The positioning member 62, on the other hand, is not a solid rod but rather is constituted by an elastic axially compressed tube 66 of a biocompatible plastic material, e.g., Silastic or the like, and a wire or tension member 67 of platinum or other biocompatible metallic or high strength plastic or fibrous material extending longitudinally slidably through the tube 66 for the purpose of imparting stiffness to the tube. The tube 66 even in its compressed state is somewhat longer than the array of electrodes 65.

As shown, the connection 63 between the leading end region 62a of the positioning member 62 and the leading end region 61a of the electrode carrier 61 is effected by the leading end region of the wire 67 which protrudes from the leading end of the tube 66. The wire has a reverse bend 67a formed therein to define a hook-like portion the free end of which is secured, as shown at 67b, to the tip of the electrode carrier, e.g., by being molded thereinto. The bend 67a in the wire 67 at the same time constitutes a hinge portion about which the positioning member 62, under conditions to be described presently, can move angularly (pivotally) relative to the electrode carrier in the common axial plane of the assembly.

The connection 64 between the trailing end region 62b of the positioning member and the trailing end region 61b of the electrode carrier is effected by having the trailing end region 66b of the tube 66 fixedly secured, e.g., bonded, to the electrode carrier as shown at 68. The trailing end region of the wire 67 extends somewhat beyond the trailing end of the compressed tube and is initially held fast to the electrode carrier, e.g., by being clamped thereto (not shown) adjacent the location of the connection 64. In the starting condition of the assembly 60, therefore, the wire 67 maintains the compressed tube straight and in close parallel juxtaposition to the side region of the electrode carrier opposite to the side region where the electrodes 65 are exposed and thereby prevents the tube from expanding.

The initial insertion of the assembly 60 into the cochlea 32 (see FIG. 23) is effected, as before, through the round window 38 with both the electrode carrier 61 and the positioning member 62 in their straight state. During this phase of the insertion operation, for which the pushing force is applied by the surgeon to the electrode carrier, the trailing end of the wire 67 remains clamped to the electrode carrier, so that the wire is constrained against movement relative to the electrode carrier and ensures that the compressed tube also remains straight. When the assembly then enters the spirally curved section of the cochlea (see FIG. 24), both the positioning member 62 and the electrode carrier 61 become correspondingly curved as the positioning member rides along the radially outer wall 44 of the cochlea, during which time the electrode carrier (because of its previously described "memory" and tendency to return to its straight form and hug the outer wall of the cochlea) closely follows the curvature of the positioning member. The contact faces of the electrodes 65 are, consequently, disposed out of the desired close proximity to the radially inner wall 43 of the cochlea and the adjacent ganglion cells 40.

When the insertion operation has been carried out to the fullest extent possible, the assembly 60 over its entire length will be positioned as is shown in FIG. 24 for the leading end region thereof, i.e., with the electrodes 65 still positioned relatively far away from the ganglion cells 40. At that point, the trailing end of the wire is unclamped from the electrode carrier and released. This eliminates the constraint exerted by the wire on the compressed tube 66 and permits the latter to expand longitudinally, but because both the leading and trailing end regions of the tube are stationarily connected to the electrode carrier at 63 and 64, the expansion of the tube causes it to assume an outwardly arched or bowed configuration relative to the electrode carrier with which the wire, by virtue of the hinge action of the bend 67a thereof and by virtue of the fact that a portion of the trailing end region of the wire is drawn into the tube as it expands and becomes longer, does not interfere. As a result, the expanding tube acts in the manner of a spring and, aided by the stiffening effect of the wire confined within the tube, exerts an outward force on the radially outer wall of the cochlea which causes the electrode carrier along its entire length to be forced across the width of the scala tympani, as indicated by the arrows in FIG. 25, until its concavely curved side region where the contact faces of the electrodes are located comes into contact with the radially inner wall of the cochlea and into close hugging contact with the modiolus, as shown in FIG. 25. The bowed or arched positioning member 62 not only serves to dispose the electrodes in the closest possible proximity to the ganglion cells, but also, once the trailing end region of the wire outside the tube has been re-clamped to the electrode carrier, locks the assembly, and especially the electrode carrier, in place and makes any instability or inadvertent movement thereof in the cochlea effectively impossible.

Figure 26:
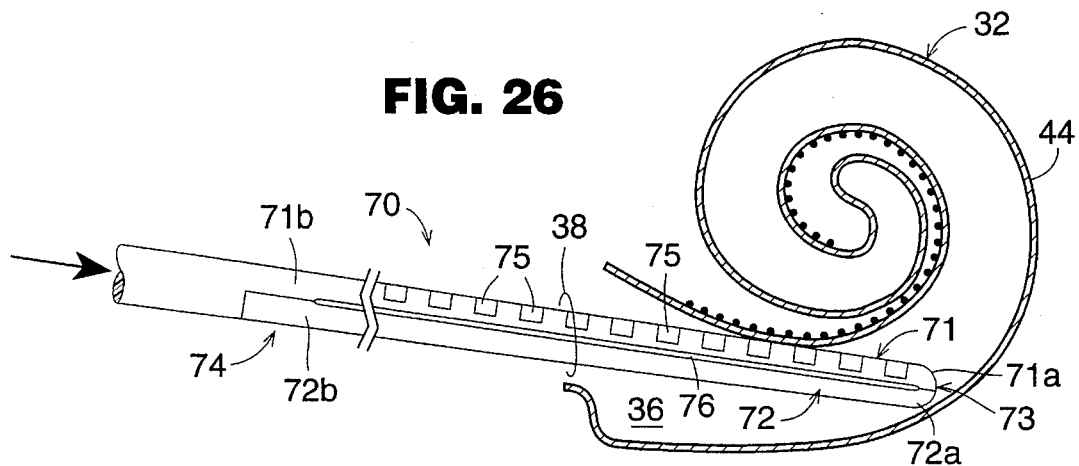
FIGS. 26, 27 and 28 are schematic illustrations in longitudinal section, respectively, of the initial, intermediate and final stages of the insertion of a cochlear electrode carrier and positioning member assembly according to a third embodiment of the present invention into the cochlea of a human ear, with FIG. 28 showing the satisfactory final locked position of the electrode carrier.
Figure 27:
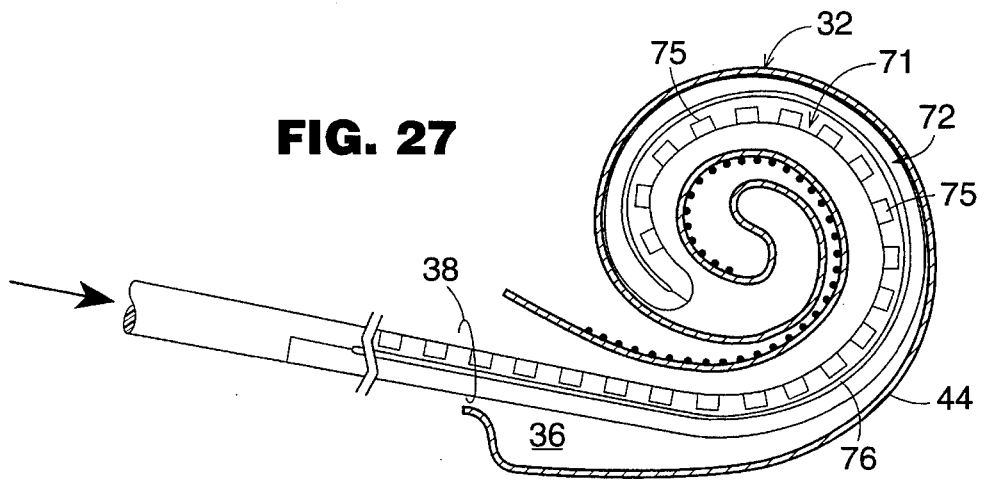
Figure 28:
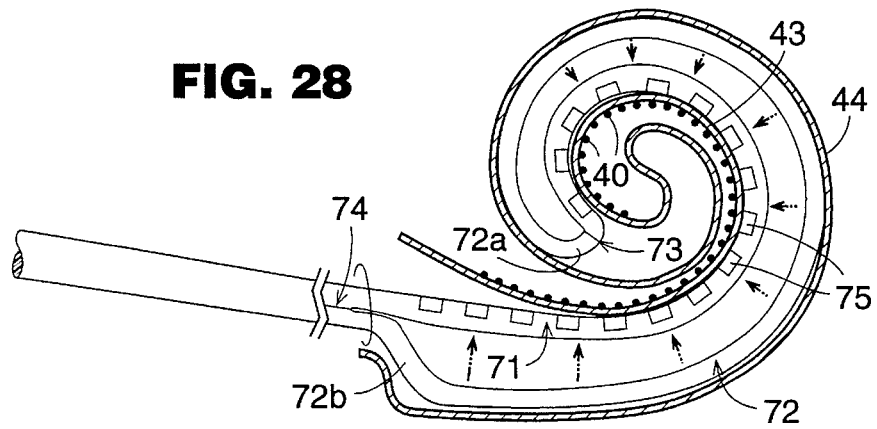

Referring now to FIGS. 26–28, in the embodiment of the invention there shown the electrode carrier/positioning member assembly 70 is a composite straight rod-like structure one part of which constitutes the electrode carrier 71 and another part of which constitutes the positioning member 72, the electrode carrier and the positioning member having their respective leading end regions 71a and 72a and their respective trailing end regions 71b and 72b connected to each other, e.g., by bonding or molding, at 73 and 74. The arrangement preferably is such that, with the positioning member 72 being located along the side region of the electrode carrier 71 opposite to the side region of the latter where the contact faces of the electrodes 75 are exposed, a small space 76 is left between and separates the medial regions of the electrode carrier and the positioning member from each other (although the presence of such a space is not essential as long as the two medial regions are not connected to each other). In the assembly 70, the electrode carrier 71 is as usual made of a biocompatible plastic material such as Silastic silicone polymer which does not have the property of swelling or expanding when exposed to water in the patient's body fluids. The positioning member 72, however, is made of a biocompatible plastic material which may also be Silastic silicone polymer but is compounded, e.g., by being admixed with finely ground NaCl, polyacrylic acid, or a like substance, so as to have the property of swelling or expanding when exposed to the water in the patient's body fluids.

The assembly 70 is initially inserted into the scala tympani through the round window 38 while in its straight state (see FIG. 26). When the leading end region 72a of the positioning member 72 reaches the radially outer wall 44 of the cochlea and the assembly enters into the spirally curved section of the cochlea, the continuing pushing force exerted on the assembly by the surgeon causes the assembly to assume the curvature of the radially outer wall 44 of the cochlea. Both the electrode carrier 71 and the positioning member 72 thereby become correspondingly curved while the former remains in close proximity to the latter, so that the electrodes 75 are disposed out of the desired degree of proximity to the modiolus and the ganglion cells 40, as shown in FIG. 27. Once the insertion operation has been carried out to its fullest extent, which is diagrammatically represented by FIG. 27, no further action by the surgeon is required in order shift the electrode carrier out of its then achieved position. Rather, the implanted assembly 70 will then be exposed to the patient's body fluids, and over a period of time the positioning member will expand. By virtue of the fixed connections 73 and 74 between the electrode carrier 71 and the positioning member 72, this expansion causes the leading and trailing end regions 72a and 72b of the positioning member to curve away from the outer wall of the cochlea (see FIG. 28), and that in turn forces the electrode carrier across the width of the scala tympani, as indicated by the arrows in FIG. 28, toward and against the radially inner wall 43 of the cochlea so as to dispose the electrode-bearing surface of the electrode carrier along its entire length in close hugging contact with the modiolus. That brings the electrodes 75 into as close a juxtaposition to the ganglion cells 40 as possible.

In summary, therefore, the present invention provides a self-positioning cochlear electrode implant assembly adapted to be implanted in the scala tympani of the spirally curved cochlea of a human ear for stimulating cells of the spiral ganglion, which assembly comprises the following features: (1) a rod-shaped cochlear electrode carrier which is made of a biocompatible plastic material and is sufficiently flexible to be able to assume the spiral curvature of the cochlea, and which has leading and trailing end regions and is tapered in cross-section from its trailing end region to its leading end region; (2) an array of cochlear electrode elements supported by the electrode carrier at respective longitudinally spaced locations thereon in a medial region of the electrode carrier between its leading and trailing end regions, the electrode elements having respective contact faces exposed along a first longitudinal side region of the electrode carrier; (3) a rod-shaped positioning member for the electrode carrier, which positioning member is also made of a biocompatible plastic material and is sufficiently flexible to be able to assume the spiral curvature of the cochlea, and which has leading and trailing end regions and is juxtaposed to and extends lengthwise of the electrode carrier along a second longitudinal side region of the latter opposite the first longitudinal side region thereof so as to have the leading and trailing end regions of the positioning member located adjacent the leading and trailing end regions, respectively, of the electrode carrier; and (4) means connecting the leading and trailing end regions of the positioning member to the leading and trailing end regions, respectively, of the electrode carrier so as to leave a medial region of the positioning member separated from the medial region of the electrode carrier and adapted to assume an arched configuration relative to the medial region of the electrode carrier. The overall arrangement of the assembly is such that, (5) upon insertion of the assembly into the scala tympani with the positioning member engaging and closely following the curvature of the radially outer wall of the cochlea and with the electrode carrier juxtaposed to and closely following the curvature of the positioning member, the latter when assuming its arched configuration against the constraint of the radially outer wall of the cochlea exerts a force on the electrode carrier at the leading and trailing end regions thereof to shift the electrode carrier into engagement at its first longitudinal side region with the radially inner wall of the cochlea so as to position the contact faces of the array of electrode elements in close proximity to the spiral ganglion cells of the cochlea; and (6) the connection between the trailing end region of the electrode carrier and the trailing end region of the positioning member serves, when the insertion of the assembly into the cochlea has been completed and the positioning member is in its arched configuration, to stabilize the assembly in and lock the same against inadvertent reverse movement out of the cochlea.

It will be understood that the foregoing description of a number of embodiments of the present invention is for purposes of illustration only, and that the various structural and operational features and relationships herein disclosed are susceptible to a number of modifications and changes none of which entails any departure from the spirit and scope of the present invention as defined in the hereto appended claims.

What is claimed is:

1. A self-positioning cochlear electrode implant assembly adapted to be implanted in the scala tympani of the spirally curved cochlea of a human ear for stimulating cells of the spiral ganglion, said assembly comprising:

a rod-shaped cochlear electrode carrier made of a biocompatible plastic material and sufficiently flexible to be able to assume the spiral curvature of the cochlea, said electrode carrier having leading and trailing end regions and tapering in cross-section from said trailing end region to said leading end region; an array of cochlear electrode elements supported by said electrode carrier at respective longitudinally spaced locations thereon in a medial region of said electrode carrier between said leading and trailing end regions thereof, said electrode elements having respective contact faces exposed along a first longitudinal side region of said electrode carrier; a rod-shaped electrode carrier-positioning member made of a biocompatible plastic material and sufficiently flexible to be able to assume the spiral curvature of the cochlea, said positioning member having leading and trailing end regions and being juxtaposed to and extending lengthwise of said electrode carrier along a second longitudinal side region of the latter opposite said first longitudinal side region thereof so as to have said leading and trailing end regions of said positioning member located adjacent said leading and trailing end regions, respectively, of said electrode carrier; and means connecting said leading and trailing end regions of said positioning member to said leading and trailing end regions, respectively, of said electrode carrier so as to leave a medial region of said positioning member separated from said medial region of said electrode carrier and adapted to assume an arched configuration relative to said medial region of said electrode carrier upon insertion of the assembly into the cochlea;

whereby, upon insertion of said assembly into the scala tympani with said positioning member engaging and closely following the curvature of the radially outer wall of the cochlea and with said electrode carrier juxtaposed to and closely following the curvature of said positioning member, said positioning member when assuming said arched configuration against the constraint of the radially outer wall of the cochlea exerts a force on said electrode carrier at said leading and trailing end regions thereof to shift said electrode carrier into engagement of said first longitudinal side region thereof with the radially inner wall of the cochlea so as to position said contact faces of said array of electrode elements in close proximity to the spiral ganglion cells of the cochlea; and said means connecting said trailing end region of said electrode carrier and said trailing end region of said positioning member further serves, when the insertion of said assembly into the cochlea has been completed and said positioning member is in said arched configuration thereof, to stabilize said assembly in and lock the same against inadvertent reverse movement out of the cochlea.

2. A cochlear electrode implant assembly according to claim 1, wherein said means for connecting said trailing end regions of said electrode carrier and said positioning member to each other comprises a fitting having a body which, when said electrode carrier and said positioning member are in side by side relation to each other, surrounds and accommodates said trailing end regions of said electrode carrier and said positioning member; and said body of said fitting has a forward end at which a portion of said fitting constitutes means enabling said positioning member, after the same has been moved forwardly through said fitting and relative to said electrode carrier to assume said arched configuration, to be locked against a reverse movement relative to said electrode carrier that would permit said positioning member to return to its side by side relation with said electrode carrier.

3. A cochlear electrode implant assembly according to claim 1, wherein said means for connecting said trailing end regions of said electrode carrier and said positioning member to each other comprises a fitting having a body with at least partly arcuate exterior peripheral portions, forward and rearward ends, and an interior partition extending from one end of said body to the other to provide said fitting with first and second substantially parallel passageways extending therethrough for accommodating said electrode carrier and said positioning member, respectively; the portion of said body of said fitting which in conjunction with said partition defines one of said first and second passageways is permanently affixed to the respective one of said electrode carrier and said positioning member extending through said one passageway; the portion of said body of said fitting which in conjunction with said partition defines the other of said first and second passageways is dimensioned for permitting sliding relative movement between said fitting and the respective other of said electrode carrier and said positioning member extending through said other passageway; and said portion of said body of said fitting in which said other passageway is located is provided with means enabling said other of said electrode carrier and said positioning member to be locked against movement through said other passageway.

4. A cochlear electrode implant assembly according to claim 3, wherein said second passageway is dimensioned to permit sliding relative movement between said fitting and said positioning member, and the portion of said body of said fitting in which said second passageway is located is provided with said means enabling said positioning member to be locked against movement through said second passageway.

5. A cochlear electrode implant assembly according to claim 3 or 4, wherein the portion of said body of said fitting in which said first passageway is located is permanently fixed to said electrode carrier.

6. A cochlear electrode implant assembly according to claim 3 or 4, wherein said portion of said body of said fitting in which said second passageway is located is provided with unidirectionally acting means permitting forward movement but preventing reverse movement of said positioning member through said second passageway.

7. A cochlear electrode implant assembly according to claim 6, wherein said unidirectionally acting means comprises a strip member supported by and extending forwardly from said portion of said body of said fitting in which said second passageway is located, said strip member being inclined toward the axis of said second passageway and having a forward end edge which is in sliding engagement with a first surface region of said positioning member when the latter moves forwardly through said second passageway, said forward end edge of said strip member being sufficiently sharp to bite into said first surface region of said positioning member and thereby wedge said positioning member against reverse movement through said second passageway substantially immediately upon start of such reverse movement.

8. A cochlear electrode implant assembly according to claim 7, wherein said strip member is supported by and extends forwardly from said partition at an inclination toward the axis of said second passageway.

9. A cochlear electrode implant assembly according to claim 8, wherein strip member is supported by said partition adjacent the rearwardmost end of said partition and extends forwardly therefrom within the confines of said second passageway.

10. A cochlear electrode implant assembly according to claim 9, wherein said strip member is welded to said partition.

11. A cochlear electrode implant assembly according to claim 9, wherein said strip member is an integral extension of said partition at said rearwardmost end of said partition and is bent over therefrom into said second passageway.

12. A cochlear electrode implant assembly according to claim 9, wherein said portion of said body of said fitting in which said second passageway is located has a forward end edge which is spaced from said forward end edge of said strip member and in sliding engagement with a second surface region of said positioning member, and which is sufficiently sharp to bite into said second surface region of said positioning member and thereby assist in wedging said positioning member against reverse movement through said second passageway substantially immediately upon start of such reverse movement.

13. A cochlear electrode implant assembly according to claim 1, wherein each of said electrode carrier and said positioning member has the form of a solid rod; and means connecting said leading end regions of said electrode carrier and said positioning member to each other comprises a ball-and-socket joint including a ball component and a correspondingly configured socket component each provided on a respective one of said electrode carrier and said positioning member.

14. A cochlear electrode implant assembly according to claim 13, wherein said ball component of said joint is located on said electrode carrier, and said socket component of said joint is located on said positioning member.

15. A cochlear electrode implant assembly according to claim 14, wherein said ball component of said joint comprises a plurality of bundled wires of a biocompatible metallic material which at a first end region thereof are embedded in said electrode carrier and which project from said leading end region of said electrode carrier generally longitudinally thereof, and said bundled wires exteriorly of said electrode carrier terminate in a second end region and thereat support a ball member; said socket component of said joint comprises an axial rearwardly extending slit provided in said leading end region of said positioning member in a common axial plane of both said positioning member and said electrode carrier, and a ball member-receiving surface recess or depression provided on said positioning member on a side region of the latter which is directed away from said electrode carrier and at a location straddling said slit, said slit being dimensioned to accommodate the portion of said bundled wires between said first and second end regions of the latter; and said joint is established by said portion of said bundled wires being received in said slit and said ball member being received and seated in said recess or depression.

16. A cochlear electrode implant assembly according to claim 1, wherein each of said electrode carrier and said positioning member has the form of a solid rod; said means connecting said trailing end regions of said electrode carrier and said positioning member to each other comprises a tubular fitting having a body provided with an internal generally axial partition and defining on opposite sides of said partition first and second substantially parallel passageways extending through and generally axially of said tubular fitting for accommodating said electrode carrier and said positioning member, respectively; the portion of said body of said tubular fitting which defines said first passageway is permanently fixed to said electrode carrier for joint movement of said tubular fitting with said electrode carrier; the portion of said body of said tubular fitting which defines said second passageway is dimensioned to permit sliding movement of said positioning member relative thereto; and said tubular fitting is provided with means adapted to be activated upon completion of the insertion of said assembly into the cochlea for immobilizing said positioning member in said arched configuration thereof against reverse movement of said positioning member relative to said tubular fitting and for thereby stabilizing said assembly in the cochlea.

17. A cochlear electrode implant assembly according to claim 16, wherein the portion of said body of said tubular fitting which defines said second passageway is deformable to permit crimping thereof onto said positioning member, and said deformable portion of said body of said tubular fitting constitutes said means activatable for immobilizing said positioning member.

18. A cochlear electrode implant assembly according to claim 17, wherein said tubular fitting comprises a length of wire spirally wound to define both an outer wall of said body of said tubular fitting and said internal partition thereof between said first and second passageways.

19. A cochlear electrode implant assembly according to claim 16, wherein the portion of said body of said tubular fitting which defines said internal partition thereof is provided with a unidirectionally acting structure extending from said partition toward the axis of said second passageway for engagement with said positioning member when the latter is accommodated in said second passageway, said unidirectionally acting structure is arranged to permit forward movement and to block reverse movement of said positioning member through said second passageway, and said unidirectionally acting structure constitutes said means activatable for immobilizing said positioning member.

20. A cochlear electrode implant assembly according to claim 19, wherein said unidirectionally acting structure comprises a strip member projecting forwardly from said partition and inclined at an angle toward said axis of said second passageway, said strip member having a forward edge which does not interfere with forward movement of said positioning member through said second passageway but which is able to bite into said positioning member for blocking any reverse movement of the latter.

21. A cochlear electrode implant assembly according to claim 20, wherein said tubular fitting comprises a strip of metal wound to define both an outer wall of said body of said tubular fitting and said internal partition thereof between said first and second passageways, and the portion of said strip which constitutes said partition has a lateral angularly inclined extension which constitutes said strip member.

22. A cochlear electrode implant assembly according to claim 1, wherein said electrode carrier has the form of a solid rod; said positioning member comprises an elastic axially compressed tube the length of which between its leading and trailing end regions in its compressed state is somewhat greater than the length of said array of electrode elements on said electrode carrier, and a flexible tension member extending slidably through said tube and having first and second end regions projecting from said tube at said leading and said trailing end regions, respectively, of said tube; said means for connecting said leading end regions of said electrode carrier and said positioning member to each other comprises a fixed connection between said first end region of said tension member and said leading end region of said electrode carrier; and said means connecting said trailing end regions of said electrode carrier and said positioning member to each other comprises a fixed connection between said trailing end region of said tube and said trailing end region of said electrode carrier, and means for releasably attaching said second end region of said tension member to said electrode carrier outside and somewhat rearwardly of said fixed trailing end region of said tube;

whereby said attaching means, when activated with said tension member straight prior to the insertion of said assembly into the cochlea, serves to maintain said positioning member in close juxtaposition to said electrode carrier while permitting both said electrode carrier and said positioning member jointly to assume the curvature of the cochlea; when deactivated after insertion of said assembly into the cochlea, serves to release said tension member so as to permit said tube, while stiffened by said tension member, to expand and assume said arched configuration and to shift said electrode carrier within the cochlea so as to juxtapose said contact faces of said array of electrode elements to the spiral ganglion cells; and when reactivated with said positioning member in said arched configuration thereof, serves to immobilize said tension member so as to maintain said positioning member in said arched configuration for thereby to stabilizing said assembly in the cochlea.

23. A cochlear electrode implant assembly according to claim 22, wherein said tension member is a wire of a biocompatible metal.

24. A cochlear electrode implant assembly according to claim 1, wherein each of said electrode carrier and said positioning member has the form of a solid rod, said electrode carrier being made of a biocompatible plastic material which is resistant to swelling or expanding when exposed to water, and said positioning member being made of a biocompatible plastic material which has the property of swelling or expanding when exposed to water; and said means connecting said leading and trailing end regions of said electrode carrier to said leading and trailing end regions, respectively, of said positioning member comprise a pair of fixed connections therebetween;

whereby during the insertion of said assembly into the cochlea, said electrode carrier and said positioning member remain in close juxtaposition to each other and jointly assume the curvature of the cochlea; after the insertion, upon said assembly being exposed over a period of time to the action of the water in the person's body fluid present in the cochlea, said positioning member expands and assumes said arched configuration and shifts said electrode carrier within the cochlea so as to juxtapose said contact faces of said array of electrode elements to the spiral ganglion cells; and said positioning member in said arched configuration serves to immobilize said assembly for stabilizing the same in the cochlea.

25. A cochlear electrode implant assembly according to claim 24, wherein said fixed connections between said electrode carrier and said positioning member are molded or bonded joints.

* * * * *